US008202225B2

(12) United States Patent
Peretto et al.

(10) Patent No.: US 8,202,225 B2
(45) Date of Patent: Jun. 19, 2012

(54) NONINVASIVE METHOD AND APPARATUS FOR MEASURING BLOOD PRESSURE BY DETERMINING A MAXIMUM FREQUENCY OF SPECTRAL CONTENT OF THE SECOND HEART SOUND

(75) Inventors: Lorenzo Peretto, Rovigo (IT); Alberto Bauer, Marbella/Malaga (ES); Andrea Mollo, Ferrara (IT)

(73) Assignee: Luca Longhini, Ferrara (IT)

( * ) Notice: Subject to any disclaimer, the term of this patent is extended or adjusted under 35 U.S.C. 154(b) by 966 days.

(21) Appl. No.: 12/199,217

(22) Filed: Aug. 27, 2008

(65) Prior Publication Data

US 2009/0062665 A1 Mar. 5, 2009

Related U.S. Application Data

(60) Provisional application No. 60/968,440, filed on Aug. 28, 2007.

(51) Int. Cl.
*A61B 5/02* (2006.01)

(52) U.S. Cl. ............... 600/528; 600/485; 600/508

(58) Field of Classification Search ............... None
See application file for complete search history.

(56) References Cited

U.S. PATENT DOCUMENTS

| 6,050,950 | A | 4/2000 | Mohler |
| 6,368,283 | B1 | 4/2002 | Xu et al. |
| 6,869,404 | B2 * | 3/2005 | Schulhauser et al. ......... 600/528 |
| 2003/0120159 | A1 | 6/2003 | Mohler |
| 2004/0167417 | A1 | 8/2004 | Schulhauser et al. |

FOREIGN PATENT DOCUMENTS

| WO | WO 02/19911 A2 | 3/2002 |
| WO | WO 2007/015153 A2 | 2/2007 |

OTHER PUBLICATIONS

Carlo Longhini, et al, "A New Noninvasive Method for Estimation of Pulmonary Arterial Pressure in Mitral Stenosis," *The American Journal of Cardiology*, vol. 68, (Aug. 1, 1991) pp. 398-401.
J. Xu et al., "A New, Simple, and Accurate Method for Non-Invasive Estimation of Pulmonary Arterial Pressure," www.hearjnl.com, (*Heart* 2002) vol. 88; pp. 76-80.
S. Aggio et al. "Noninvasive Estimation of the Pulmonary Systolic Pressure From the Spectral Analysis of the Second Hear Sound,"; *Acta Cardiologica*, vol. XLV, 1990, 3 pp. 199-202.
Danmin Chen, et al., "Estimation of Pulmonary Artery Pressure by Spectral Analysis of the Second Heart Sound," *The American Journal of Cardiology*, vol. 78, (Oct. 1, 1996) pp. 785-789.
B. Popov et al. "Automated Extraction of Aortic and Pulmonary Components of the Second Heart Sound for the Estimation of Pulmonary Artery Pressure," *Conference Proceedings 26th Annual International Conference of The IEEE Engineering in Medicine and Biology Society* (IEEE Cat. No. 04CH37558) IEEE, Piscataway, NJ, USA. vol. 2, 2004, pp. 921-924. ISBN: 0-7803-8439-3.
International Search Report corresponding to PCT/IB2006/002111 dated Jan. 24, 2007.
International Search Report for PCT International Application No. PCT/IB2008/002236, mailed Jan. 22, 2009.

* cited by examiner

*Primary Examiner* — Tracy Vivlemore
(74) *Attorney, Agent, or Firm* — RatnerPrestia (57) ABSTRACT

Methods and apparatus for noninvasively estimating a blood pressure are provided. A bandpass filter is applied to a second heart sound (S2) component to generate a filtered S2 component. The bandpass filter has a lower cutoff frequency greater than a maximum frequency of the S2 component. The maximum frequency of the S2 component is estimated using the filtered S2 component, a predetermined relationship is applied between the estimated maximum frequency and blood pressure to generate a blood pressure estimate and the blood pressure estimate is displayed.

24 Claims, 6 Drawing Sheets

NONINVASIVE METHOD AND APPARATUS FOR MEASURING BLOOD PRESSURE BY DETERMINING A MAXIMUM FREQUENCY OF SPECTRAL CONTENT OF THE SECOND HEART SOUND

CROSS REFERENCE TO RELATED APPLICATIONS

This application is related to and claims the benefit of U.S. Provisional Application No. 60/968,440 entitled NONINVASIVE METHOD AND APPARATUS FOR MEASURING BLOOD PRESSURE BY DETERMINING A MAXIMUM FREQUENCY OF SPECTRAL CONTENT OF THE SECOND HEART SOUND filed on Aug. 28, 2007, the contents of which are incorporated herein by reference.

FIELD OF THE INVENTION

The present invention relates to the field of clinical evaluation of cardiac diseases and, more particularly, to methods and apparatus for noninvasively estimating the pulmonary artery pressure.

BACKGROUND OF THE INVENTION

Pulmonary artery pressure (PAP) measurements are known in the art and have been used for a number of years to aid in the diagnosis of cardiac and pulmonary diseases. A PAP measurement may be obtained through an invasive procedure, such as using a pulmonary arterial catheter (e.g., Swan-Ganz catheter). A PAP estimation may also be obtained through a noninvasive procedure, for example, using Doppler Echocardiography, in order to estimate the PAP via known-in-the-art ultrasound techniques. In addition, methods using heart sounds analysis have also been proposed. For example, see U.S. Pat. No. 6,368,283 to Xu et al., entitled "Method and apparatus for estimating systolic and mean pulmonary artery pressures of a patient."

Invasive procedures, however, are typically uncomfortable and problematic for the patient. Pulmonary artery catheterization, for example, even in skilled hands, may carry various risks and complications.

Doppler Echocardiography, may not be efficacious in the absence of a Doppler-detectable tricuspid valve regurgitation. Furthermore, the values of systolic PAP are only approximate because a clinical estimation of the right atrial (RA) pressure is typically necessary. This may be a potential source of error in the estimation of the real PAP in a patient. Furthermore, a good acoustic window and satisfactory flow tracing are typical factors used to adequately locate the tricuspid regurgitant jet. These factors, however, may be suboptimal in persons with pulmonary hyperinflation, or in those persons who are obese, because of poor transmission of sound waves.

Both conventional invasive and noninvasive procedures typically require highly skilled personnel (i.e., physicians or technicians) as well as the utilization of expensive equipment. Cardiac catheterization may also require use of a suitably equipped operating room, with attending operating room personnel.

SUMMARY OF THE INVENTION

The present invention is embodied in methods and apparatus for noninvasively estimating a blood pressure. The method includes the step of applying a bandpass filter to a second heart sound (S2) component to generate a filtered S2 component. The bandpass filter has a lower cutoff frequency that is greater than a maximum frequency of the S2 component. The method also includes the steps of estimating the maximum frequency of the S2 component using the filtered S2 component, applying a predetermined relationship between the estimated maximum frequency and blood pressure to generate a blood pressure estimate and displaying the blood pressure estimate.

BRIEF DESCRIPTION OF THE DRAWINGS

The invention is best understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover in the drawings, common numerical references are used to represent like features/elements. Included in the drawings are the following figures.

DETAILED DESCRIPTION OF THE INVENTION

The present invention describes methods and apparatus for noninvasively estimating blood pressure and, desirably, pulmonary artery pressure (PAP). According to the present invention, PAP may be estimated from a diastolic signal that is extracted from a phonocardiogram signal (PCG) using a simultaneously measured electrocardiogram (ECG) signal from respective PCG and ECG sensors. In general, the diastolic signal includes a second heart sound (S2) component and may include a portion of the diastolic interval. The diastolic signal may also include a portion of the systolic interval, i.e. prior to the S2 component. The S2 component may further be isolated from the diastolic signal. A maximum frequency, $F_{MAX}$, of the S2 component, is desirably estimated using a bandpass filter having a lower cutoff frequency that is greater than the maximum frequency, $F_{MAX}$. A PAP estimate may be generated using a predetermined relationship between the estimated $F_{MAX}$ and the PAP. In a further exemplary embodiment, a number of PCG and corresponding ECG signals are acquired and analyzed in order to generate the PAP estimate. Although the present invention describes methods and apparatus for PAP estimation, it is contemplated that the present invention may be used for any blood pressure measurement, such as systemic pressure, PAP being only one example of such a blood pressure measurement. It is contemplated that a predetermined relationship may be determined between an estimated $F_{MAX}$ and blood pressure to determine a blood pressure estimate.

The S2 component, generated by both the aortic and myocardium valves and by the pulmonary valve, is typically transmitted to the surrounding body, including the chest wall, through the right side of the heart, i.e., the pulmonary atrium and ventricle. Because the thickness of the left side of the heart is much greater than the thickness of the right side of the heart, the S2 component, through the left side, may be attenuated and low-pass filtered in transmission to the chest wall. Accordingly, sounds originating inside the heart may generally be transmitted to the chest wall through the right atrium and ventricle walls.

Typically, the S2 component includes an aortic (A) subcomponent, corresponding to closure of the aortic valve, and a pulmonary (P) subcomponent, corresponding to closure of the pulmonary valve. Generally, in an S2 component that is transmitted to the chest wall, the A subcomponent precedes the P subcomponent. In some instances, the P subcomponent may precede the A subcomponent or the A and P subcomponents may appear to occur simultaneously.

For the S2 component, both the aortic and pulmonary valves feature similar characteristics and biological composition. The aortic and pulmonary valves typically generate sounds with similar spectral composition. However, aortic valve sounds are mainly transmitted outside the heart through its right side walls, passing through the ventricles separation walls, which, in turn, modifies the spectral content as compared with sounds generated by the pulmonary valve. This leads to an S2 component which includes A and P subcomponents with very similar spectral content. Accordingly, the spectral content of heart sounds, generally, are a function of the elements surrounding the heart itself, such as muscle, organ walls and tissue.

The frequency spectral composition of the pulmonary valve sound is highly correlated to the PAP. Furthermore, the S2 component itself includes spectral content related to PAP. As the PAP increases, the whole spectral content of the S2 component shifts towards higher frequencies and the spectral content becomes enlarged. Accordingly, in the case of pulmonary hypertension, the S2 component is much more likely to be distorted and to have an increase in the spectral content, as compared with S2 components having lower respective PAP's. For pulmonary hypertension, the S2 component may become distorted and have an increased spectral content because of an increased number of vibration modes due to a structural change of the walls and muscles surrounding the right side of the heart. Accordingly, the inventors have determined that it may be desirable to determine the higher frequencies of the spectrum of the S2 component.

Figure 1A:
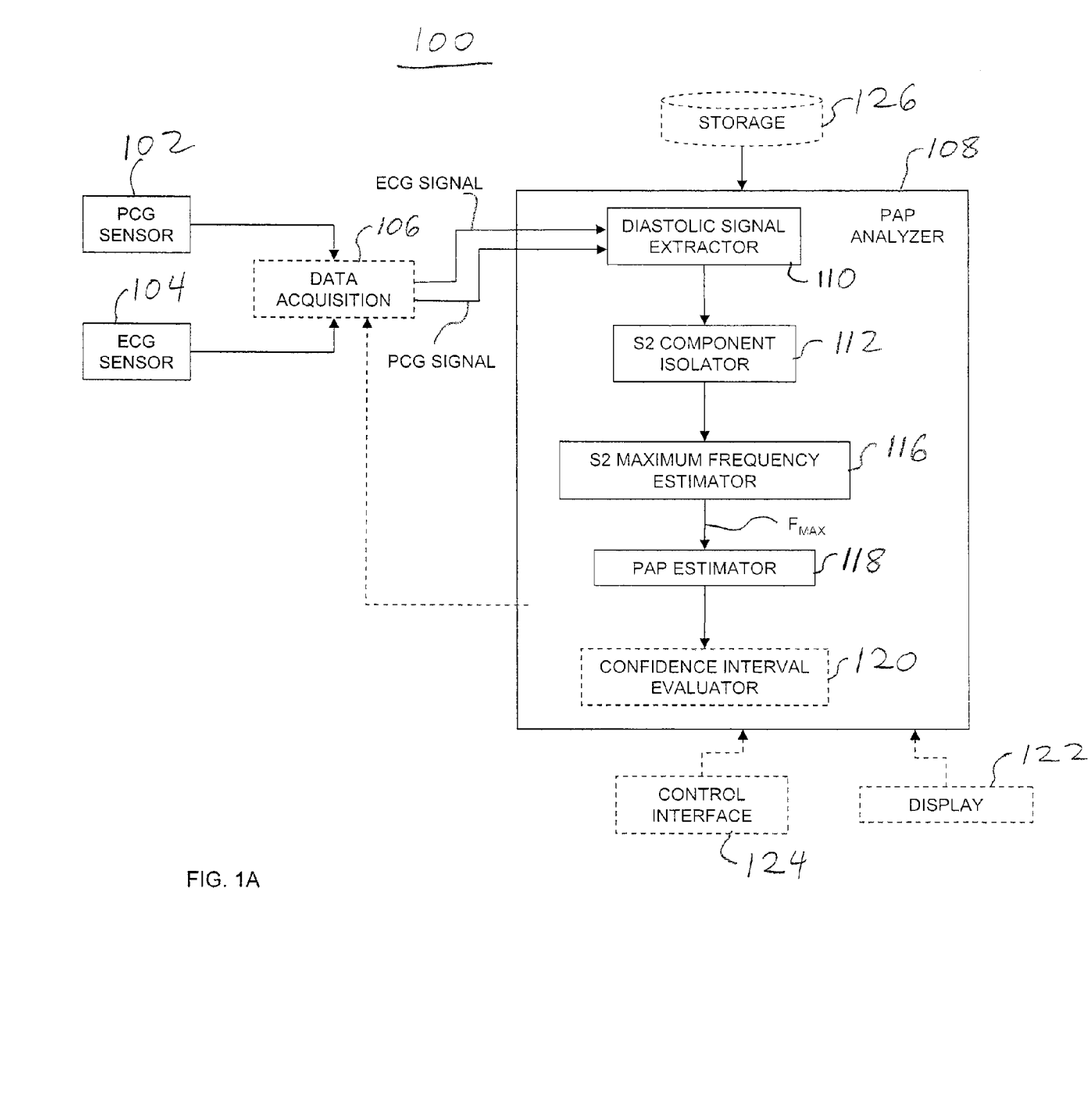
FIGS. 1A and 1B are functional block diagrams illustrating an exemplary apparatus for noninvasively estimating a pulmonary artery pressure (PAP), according to an embodiment of the present invention.
Figure 1B:
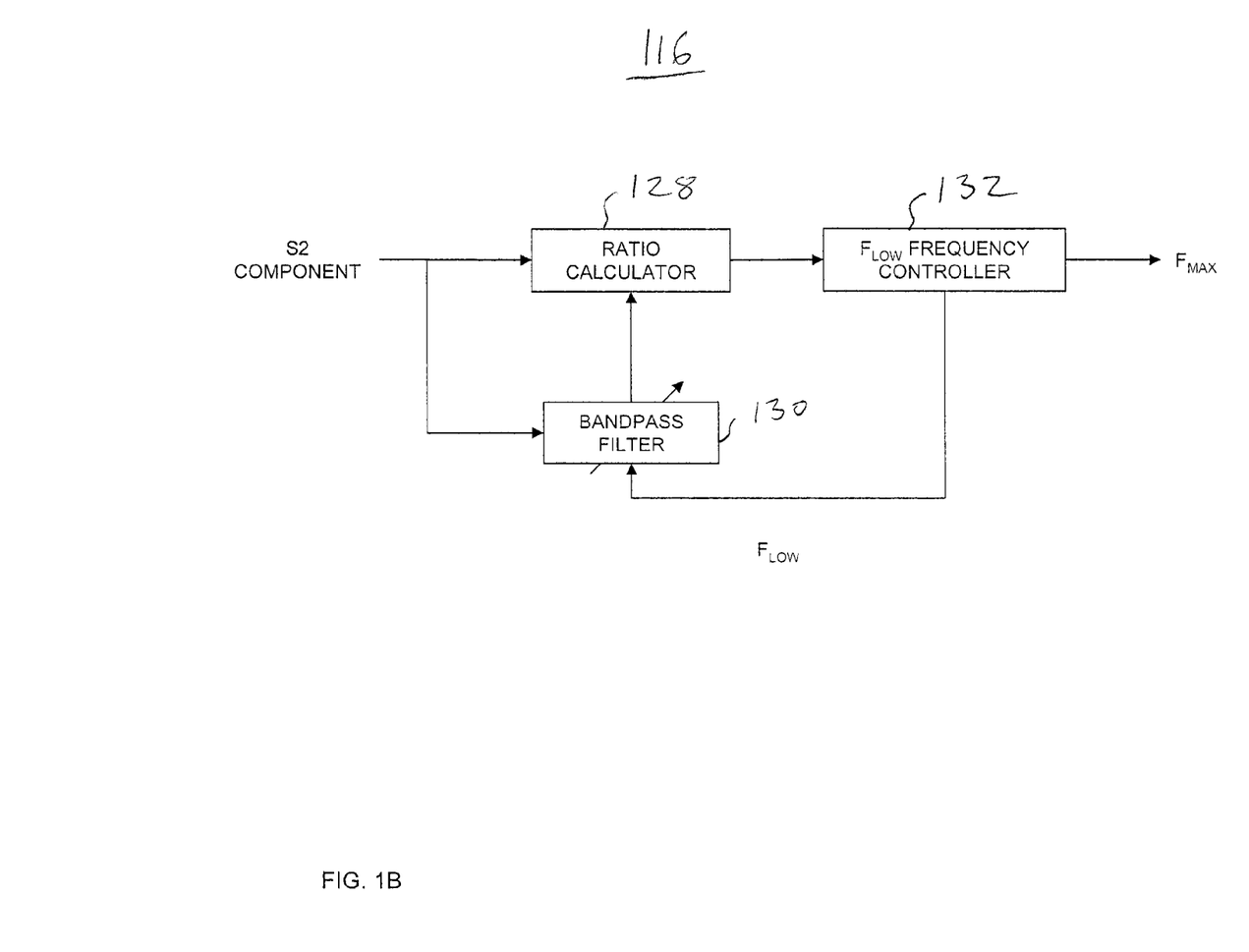

FIGS. 1A and 1B are functional block diagrams illustrating an exemplary apparatus 100 for noninvasively estimating a PAP, according to an embodiment of the present invention. More particularly, FIG. 1A is a functional block diagram of exemplary apparatus 100; and FIG. 1B is a functional block diagram of S2 maximum frequency estimator block 116 of PAP analyzer 108. The system shown in FIG. 1A includes some of the elements described in copending U.S. application Ser. No. 11/496,754 entitled NONINVASIVE APPARATUS AND METHOD FOR ESTIMATING BLOOD PRESSURE, which describes a noninvasive blood pressure measurement system.

The exemplary embodiment, however, describes apparatus and methods for noninvasively generating a PAP estimate by estimating a maximum frequency of spectral content of an S2 component. Referring to FIG. 1A, a PCG signal from PCG sensor 102 and an ECG signal from ECG sensor 104 are provided to PAP analyzer 108. PAP analyzer 108 may perform all acquisition, synchronization and digitization functions. Optionally, PCG and ECG signals may be provided to a data acquisition system 106 and data acquisition system 106 may perform some or all of the acquisition, synchronization and digitization functions.

The PCG sensor 102 may be any suitable sensor for acquiring a PCG signal and providing the PCG signal to PAP analyzer 108 or, optionally, data acquisition system 106. PCG sensor 102 may include a signal conditioner (not shown) that may provide, for example, noise reduction of background noise, a filter suitable for suppressing components outside of a typical frequency range of the PCG signal, amplification and/or impedance matching between PCG sensor 102 and PAP analyzer 108 or, optionally, data acquisition system 106. It is understood that PCG sensor 102 is provided at one or more suitable locations on the chest wall for obtaining the PCG signal.

The ECG signal is typically a multilead ECG signal. In an exemplary embodiment ECG sensor 104 consists of three electrodes having three-leads coupled to PAP analyzer 108 or, optionally, to data acquisition system 106. ECG sensor 104 may include a signal conditioner (not shown) that may amplify one or more differential voltages among or between multiple ECG electrodes. It is understood that the ECG sensor 104 may include any desired number of electrodes for obtaining appropriate ECG signals to determine a QRS complex. It is understood that the ECG electrodes are provided at suitable locations on the chest wall for obtaining the multilead ECG signal.

Examples of a suitable data acquisition system 106, PCG sensor 102, ECG sensor 104, and PCG/ECG signal conditioners are described copending U.S. application Ser. No. 11/496,754 entitled NONINVASIVE APPARATUS AND METHOD FOR ESTIMATING BLOOD PRESSURE.

It is contemplated that PAP analyzer 108 may include any computer including a processor for generating a PAP estimate from the digitized ECG and digitized PCG signals using an algorithm in accordance with the subject invention. The PAP analyzer 108 may include electronic components and any software suitable for performing at least part of the functions of generating a PAP estimate.

PAP analyzer 108 desirably generates a PAP estimate using the PCG and corresponding ECG signals respectively received from PCG sensor 102 and ECG sensor 104 or, optionally, from data acquisition system 106. The PAP analyzer includes a diastolic signal extractor 110 that is configured to extract a diastolic signal from the received PCG signal using the received ECG signal. In one exemplary embodiment, two consecutive QRS complexes are identified in the ECG signal and used to provide a timing window for extracting the diastolic signal from the PCG signal (described further below). The extracted diastolic signal is provided to S2 component isolator 112.

S2 component isolator 112 desirably isolates an S2 component from the extracted diastolic signal. The isolated S2 component desirably includes the A subcomponent and the P subcomponent, discussed above. The diastolic signal may include an isoelectric signal component, where the isoelectric signal component refers to a part of the diastolic signal without significant S2 component information. The isoelectric signal component may have a constant bias but may include a noise component. If a fixed time interval is used to extract the S2 component, the isoelectric signal component may contribute the estimation of $F_{MAX}$ and, thus, may cause the PAP estimate to be incorrect. Accordingly, it is desirable to reduce the influence of the isoelectric signal component on the PAP estimate. S2 component isolator 112 receives the extracted diastolic signal from diastolic signal extractor 110 and determines a target interval from the extracted diastolic signal such that the target interval includes the S2 component. S2 component isolator 112 may determine an onset time and an end time for the S2 component, to form the target interval, described further below. S2 component isolator 112 may use the target interval to extract, and thus isolate, the S2 component from the extracted diastolic signal. The isolated S2 component is provided to S2 maximum frequency estimator 116.

S2 maximum frequency estimator 116 desirably estimates a maximum frequency, $F_{MAX}$, from the isolated S2 component received from S2 component isolator 112. The estimated $F_{MAX}$ represents a maximum frequency of spectral content of the S2 component. As discussed above, it is known that there is a relationship between PAP and the frequency content of the S2 component. The maximum frequency, $F_{MAX}$, is related to the highest vibration modes of the heart, which are related to the value of PAP. Although the entire S2 component frequency spectrum is related to the PAP, the inventors have determined that there is a strong correlation between PAP and the highest frequencies of S2.

Referring to FIG. 1B, an isolated S2 component may be provided to each of a ratio calculator 128 and a variable bandpass filter 130. Ratio calculator 128 also receives a filtered S2 component from bandpass filter 130 and provides a ratio, associated with an amplitude of the unfiltered S2 component and the filtered S2 component, to $F_{LOW}$ frequency controller 132.

Ratio calculator 128 may generate an S2 parameter and a filtered S2 parameter associated with the respective amplitudes of the isolated S2 component (i.e., not filtered) and the filtered S2 component. In an exemplary embodiment, each of the S2 and filtered S2 parameters may be determined from a corresponding root-mean-square (rms) value, a peak value or a mean value of the absolute value. It is contemplated that any suitable value that may represent the respective amplitudes of the S2 and filtered S2 components may be used. Ratio calculator 128 may then calculate a ratio between the S2 parameter and the filtered S2 parameter and provide the ratio to $F_{LOW}$ frequency controller 132.

In an exemplary embodiment, bandpass filter 130 includes a fixed higher cutoff frequency, $F_{HIGH}$ and a variable lower cutoff frequency, $F_{LOW}$, that may be adjusted according to $F_{LOW}$ frequency controller 132. The lower cutoff frequency, $F_{LOW}$, is desirably initialized to be greater than $F_{MAX}$ to be estimated. Typically, an S2 component has a frequency range of about 20 Hz up to about 400 Hz, and, in some instances, up to about 500 Hz, depending upon the physical characteristics of the individual. $F_{MAX}$ is typically in a range of about 150-450 Hz. Although in an exemplary embodiment, $F_{HIGH}$ is fixed to about 500 Hz and $F_{LOW}$ is initialized at about 450 Hz, it is contemplated that $F_{HIGH}$ may be between about 500-550 Hz and $F_{LOW}$ may be initialized between about 400 Hz-450 Hz. An initial bandwidth of bandpass filter 130 may be between about 5 Hz to 50 Hz. Because it is desired to estimate the maximum frequency of the S2 component, it is understood that any suitable $F_{LOW}$ and $F_{HIGH}$ may be provided such that the initially filtered S2 contains higher frequencies than are typically associated with the S2 component, i.e., an initial $F_{LOW}$ greater than $F_{MAX}$.

Figure 3:
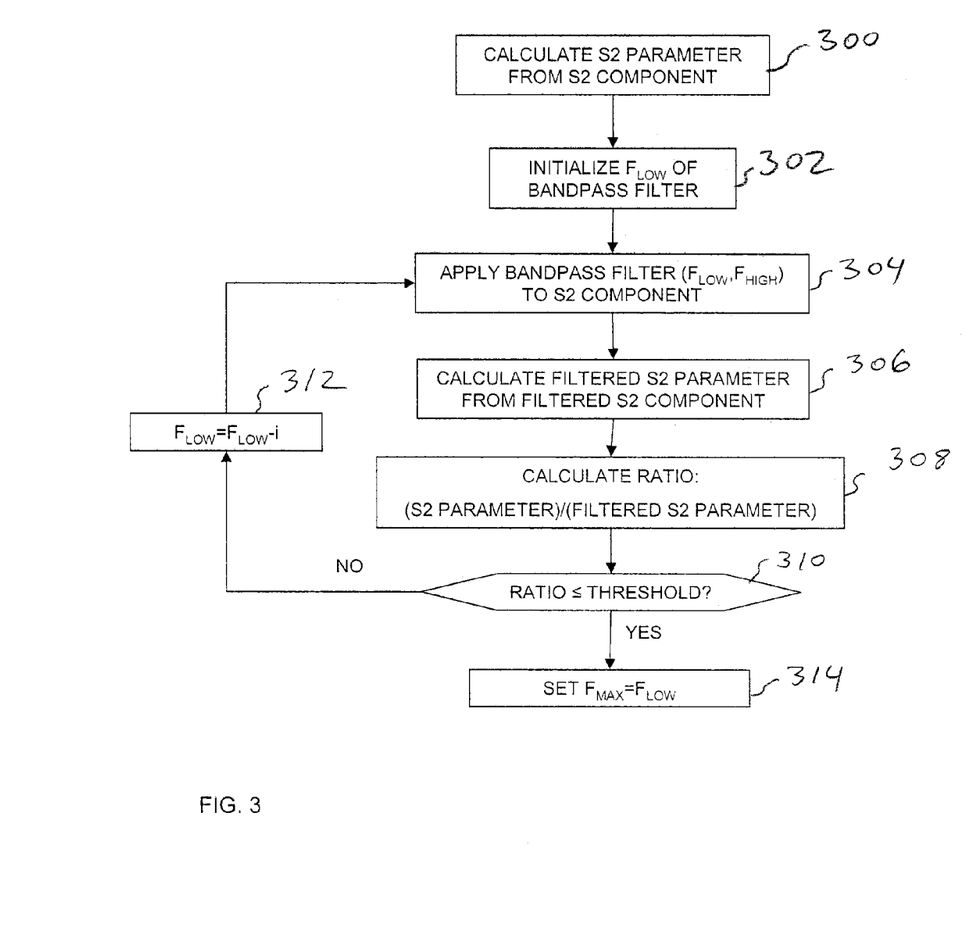
FIG. 3 is a flow chart illustrating an exemplary method for determining a maximum frequency of an S2 component, according to an embodiment of the present invention.

$F_{LOW}$ frequency controller 132 compares the ratio received from ratio calculator 128 to a predetermined threshold, and determines whether to adjust the lower cutoff frequency, $F_{LOW}$, of bandpass filter 130 or set $F_{MAX}$ equal to the currently selected $F_{LOW}$ (described further with respect to FIG. 3). $F_{LOW}$ frequency controller 132 provides the estimated maximum frequency $F_{MAX}$ to PAP estimator 118. Although in an exemplary embodiment bandpass filter 130 is a $4^{th}$ order Butterworth filter, it is understood that any bandpass filter having characteristics suitable for determining a maximum frequency of the S2 component may be used.

Referring back to FIG. 1A, PAP estimator 118 desirably generates a PAP estimate by applying a predetermined relationship between PAP and the estimated $F_{MAX}$ received from S2 maximum frequency estimator 116. The predetermined relationship is described further below. It is contemplated that the predetermined relationship may be stored in an optional storage means 126 and retrieved by PAP estimator 118 during generation of the PAP estimate. The PAP estimate may be provided to storage means 126 and/or an optional display 122.

In an exemplary embodiment, a predetermined number of PCG signals and corresponding ECG signals are respectively acquired from PCG sensor 102 and ECG sensor 104 and processed by PAP analyzer 108 in order to reduce noise artifacts that may be encountered during a single PCG signal and corresponding ECG signal acquisition. For example, noise artifacts may include respiration, patient movement, sensor movement as well as other physiological sounds and background noise that may be added to the PCG and/or ECG signals during one acquisition period. Accordingly, a predetermined number of PCG and ECG signals may be acquired. In an exemplary embodiment, the predetermined number of PCG and ECG signals includes a range of about 50-70. It is contemplated that fewer or more signals may be acquired and processed depending upon the recording conditions as well as background noise.

In an exemplary embodiment, the PAP analyzer 108 may process the predetermined number of PCG signals and corresponding ECG signals to generate a plurality of PAP estimates, described further below with respect to FIG. 5. The plurality of PAP estimates may be stored in storage means 126. PAP analyzer 108 may include a confidence interval evaluator 120 to evaluate a confidence interval measure from the plurality of PAP estimates generated using the predetermined number of acquired signals. For example, the confidence interval measure may provide high and low PAP estimates within a confidence interval from the PAP estimates. The confidence interval measure may be provided by interval evaluator 120 to storage means 126 and/or display 122. Although illustrated with respect to a plurality of PAP estimates, it is contemplated that a confidence measure may be provided for a single PAP estimate as well.

Optional display 122 may present, for example, a PAP estimate, an extracted diastolic signal, an isolated S2 component, an estimated $F_{MAX}$, a confidence interval measure, a PCG signal and/or an ECG signal. Display 122 may further present control parameters for controlling data acquisition. Control parameters may include, for example, an acquisition period duration, a number of PCG and ECG signals to be acquired and an exemplary method (described further below) for obtaining a PAP estimate from a plurality of acquired PCG and ECG signals. Display 122 may include one or more light emitting diodes (LEDs) for providing visual confirmation or error notification during the data acquisition process. It is contemplated that display 122 may include any display capable of presenting information including textual and/or graphical information. Although not shown, PAP analyzer 108 may also include an audio output for providing heart sounds and/or audible confirmation or error notification during a data acquisition process.

Optional storage means 126 may store, for example, a PAP estimate, an extracted diastolic signal, an isolated S2 component, an estimated $F_{MAX}$, a confidence interval measure, a PCG signal and/or an ECG signal. It is contemplated that storage means 126 may be a memory, a magnetic disk, a database or a further storage means on a remote device, such as a device corresponding to display 122.

PAP analyzer 108 may optionally include a control interface 124 for providing control parameters to the PAP analyzer 108 and/or for providing further control parameters to data acquisition system 106 (not shown), for example, selecting a method for obtaining a PAP estimate. Control interface 124 may further select signals to displayed and/or stored. The control interface may include a pointing device type interface for selecting control parameters, display parameters and/or storage parameters using display 122. Control interface 124 may further include a text interface for entering information regarding the acquired signals as well as patient information and a filename for storing acquired and/or analyzed data in storage means 126.

It is contemplated that the data acquisition system 106 and/or PAP analyzer 108 may be configured to connect to a network, including a global information network, e.g., the Internet (not shown) such that a generated PAP estimate, an extracted diastolic signal, an isolated S2 component, an estimated $F_{MAX}$, a confidence interval measure, a PCG signal and/or an ECG signal may be transmitted to a remote location for further processing and/or storage. Although in an exemplary embodiment PAP analyzer 108 includes an Internet connection, It is understood that transmission of acquired and analyzed data via an output port of PAP analyzer 108 may be provided by any wireless or wired connection.

In an exemplary embodiment, the data acquisition system 106 and PAP analyzer 108 may each be configured to connect to the Internet (not shown) such that data acquisition system 106 transmits PCG and ECG signals to PAP analyzer 108 via the Internet. PAP analyzer 108 receives the PCG and ECG signals from data acquisition system 106 and may transmit one or more of a PAP estimate, an extracted diastolic signal, an isolated S2 component, $F_{MAX}$ and a confidence interval to data acquisition system 106. It is understood that data acquisition system 106 may be connected to the PAP analyzer 108 via any wired or wireless connection.

Although display 122, control interface 124 and storage means 126 are shown as being connected to PAP analyzer 108, it is contemplated that one or more of display 122, control interface 124 and storage means 126 may be connected to data acquisition system 106.

A suitable PCG sensor 102, ECG sensor 104, data acquisition system 106, PAP analyzer 108, display 122, control interface 124, and storage means 126 will be understood by the skilled person from the description herein.

Figure 2:
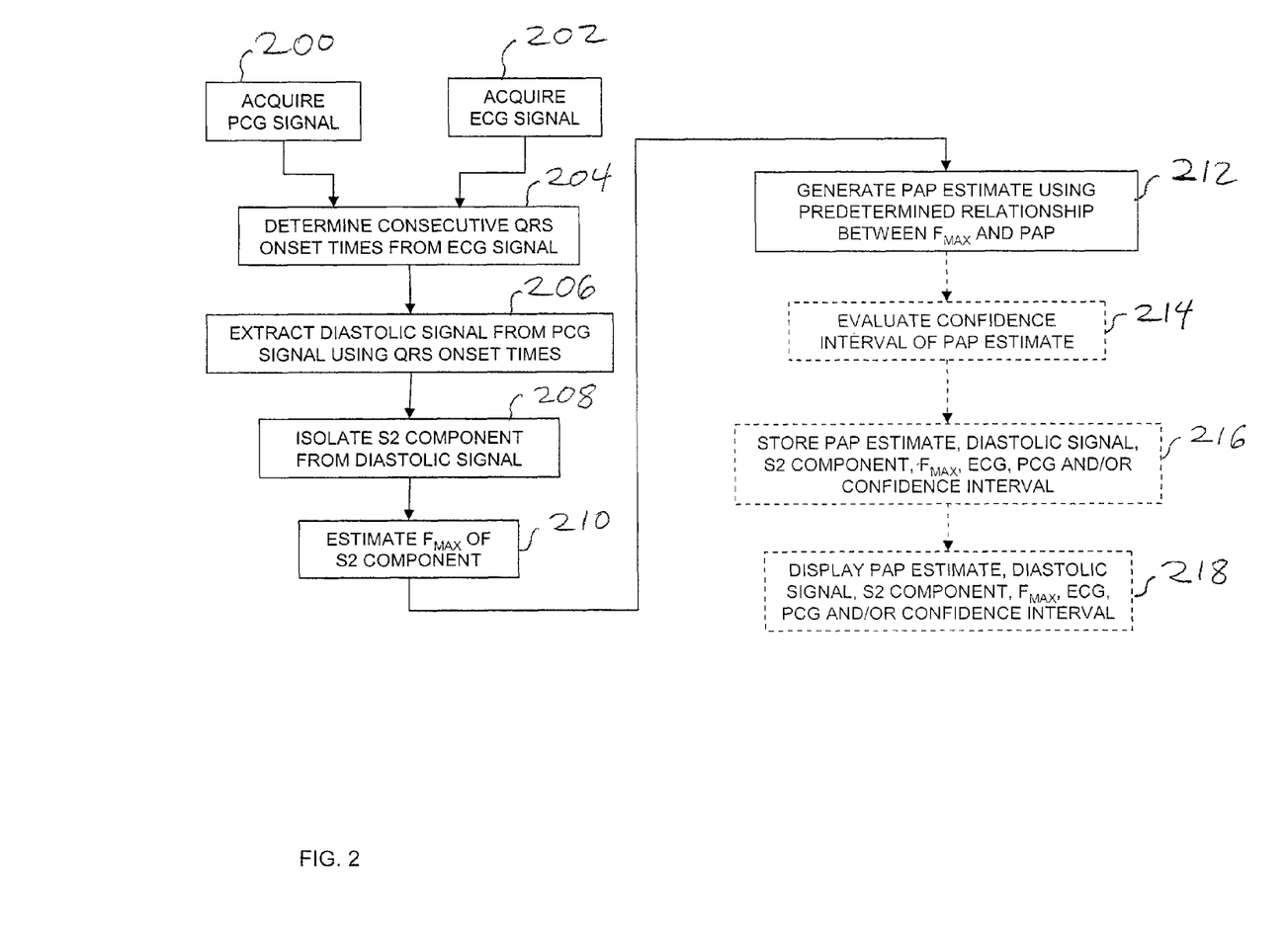
FIG. 2 is a flow chart illustrating an exemplary method for noninvasively estimating PAP, according to an embodiment of the present invention.

FIG. 2 is a flowchart illustrating an exemplary method for noninvasively estimating the PAP according to an embodiment of the present invention. In step 200, a PCG signal is acquired and in step 202 an ECG signal is acquired. The PCG signal and ECG signal are desirably synchronously acquired, for example, using PAP analyzer 108 and/or optional data acquisition system 106 with PCG sensor 102 and ECG sensor 104 (FIG. 1A).

In step 204, two consecutive QRS complex onset times are determined using known in the art techniques from the ECG signal. In an exemplary embodiment, the first two consecutive QRS complex onset times are used to extract the diastolic signal. It is understood that any pair of QRS complex onset times may be used to extract the diastolic signal. The QRS complex onset times may be used to define an interval containing a diastolic signal within the PCG signal. A first QRS complex onset time, $T_f$, and a second QRS complex onset time, $T_g$, may be determined from ECG signal.

In step 206, a diastolic signal is extracted from the PCG signal using the determined QRS complex onset times $T_f$ and $T_g$. A time interval, $T_e$, may be calculated from the two QRS complex onset times. An S2 onset time for the diastolic signal may be determined according to the calculated time interval. In an exemplary embodiment, a time interval, $T_q$, corresponding to a quarter of time interval $T_e$ may be used as the S2 onset time.

A predetermined portion of the PCG signal beginning with the S2 onset time is extracted as the diastolic signal. In an exemplary embodiment, the predetermined portion corresponds to 330 ms. The inventors have determined that a diastolic signal is included within a 330 ms portion of the PCG signal having an S2 onset time corresponding to $T_q$. In another embodiment, a duration of the predetermined portion may be determined from a relationship between the predetermined portion of the PCG signal and the time interval $T_e$ between consecutive QRS complex onset times. For example, the duration may be determined from $T_e/2$. It is contemplated that any suitable portion of the PCG signal that includes the S2 component of the diastolic signal may be used in order to extract a diastolic signal. The extracted diastolic signal may further be normalized. Steps 204 and 206 may be performed by diastolic signal extractor 110 (FIG. 1A).

In step 208, an S2 component is isolated from the diastolic signal extracted in step 206, for example, by S2 component isolator 112 (FIG. 1A). To isolate the S2 component, a portion of the extracted diastolic signal having a maximum integration value is selected and onset and end times of a target interval for the S2 component are determined. For example, the extracted diastolic signal may be separated into a number of portions according to an integration window, described below. An integration value for each portion of the diastolic signal may be determined by a summation of an absolute value of the corresponding portion of the diastolic signal in the integration window. The portion of the diastolic signal having the maximum integration value may represent a maximum energy of the diastolic signal. For digital integration, it is understood that the integration may be performed by any analog circuitry, any digital circuitry, any software or any combination thereof. It is contemplated that any number of well known numerical methods may be used to determine the integration value.

The portion of the extracted diastolic signal is selected using an integration window that desirably has a duration (i.e., from an onset time $T_1$ to an end time $T_2$), that include at least the S2 component. The S2 component may have a duration between about 70-120 ms, depending upon the characteristics of the individual. Accordingly, in an exemplary embodiment, the duration of the integration window is between about 90-150 ms, more particularly, about 100 ms. It is contemplated that any suitable duration may be used such that an integration window includes at least the S2 component.

In an exemplary embodiment, the integration is performed with respect to an absolute value of the diastolic signal and using a moving window of about 0-20 ms, more particularly 0-13 ms. It is understood that any suitable moving window may be used to determine the integration value and that use of the absolute value of the S2 component is not meant to limit the scope of the invention. For example, a squared diastolic signal may be used for the integration.

Within the integration window, the onset time $T_1$ of the integration window is increased while the end time $T_2$ of the integration window is fixed, and a first integration value is determined. The onset time $T_1$ is increased until a decrease in the first integration value from the maximum integration value is greater than or equal to a predetermined onset threshold and the adjusted onset time is set as the onset time $T_A$ of the target interval.

Similarly, the end time $T_2$ of the integration window is decreased while the onset time $T_1$ of the integration window is fixed, and a second integration value is determined. The end time $T_2$ is decreased until a decrease in the second integration value from the maximum integration value is greater than or equal to a predetermined end threshold and the adjusted end time is set as the end time $T_B$ of the target interval. The S2 component is isolated from the diastolic signal using the target interval $(T_A, T_B)$.

Although in an exemplary embodiment, the onset and end threshold are each about 5-20%, and more specifically 10%, it is contemplated that any suitable onset threshold and end threshold may be selected to reduce the influence of the isoelectric signal component for PAP estimation. Although an exemplary embodiment sets the end threshold equal to the onset threshold, it is understood that the onset threshold may be different from the end threshold.

In step 210, an $F_{MAX}$ is estimated using the isolated S2 component, for example, using S2 maximum frequency isolator 116 (FIG. 1A), described below with respect to FIG. 3.

in step 212, a PAP estimate is generated using a predetermined relationship between the estimated $F_{MAX}$ and PAP, for example with PAP estimator 118 (FIG. 1A). In one embodiment, the predetermined relationship may be approximated as a linear relationship, as shown in eq. (1):

$$\text{PAP Estimate} = b * F_{MAX} + q \text{ mmHg} \quad (1)$$

where b represents a gain constant and q represents a bias term. Parameters b and q may be determined experimentally, for example, as described below.

In an exemplary embodiment, the parameters b and q in the predetermined relationship shown in eq. (1) may be determined through known in the art curve fitting techniques, such as the least squares technique, based on PAP measurements obtained using a right-sided cardiac catheterization technique from a number of patients as well as from estimation of a number of maximum frequencies $F_{MAX}$ from the number of patients using the exemplary system 100 (FIG. 1A). It is contemplated that the predetermined relationship may be represented as a higher order linear function or a nonlinear function that may also be determined through linear regression techniques based on PAP measurements obtained using the right-sided cardiac catheterization technique. A large number of measurements may be collected from each patient in order to evaluate a measurement interval for each PAP measurement (i.e., via the catheterization technique). This procedure is in accordance with the NF ENV 13005 standard "ISO Guide to the Expression to the Uncertainty in Measurement," Geneva, Switzerland, 1995, which prescribes the evaluation of the statistical mean value and of the standard uncertainty of a measurement gauged by means of experimental results. According to the exemplary embodiment, the standard uncertainty is given by kS, where k is the coverage factor and S is the estimate of the standard deviation a associated with the expected value:

$$S = \sqrt{\frac{1}{N}\sum_{n=1}^{N}(PAP_n - \mu)^2} \quad (2)$$

where $PAP_n$ the generic $n^{th}$ PAP evaluated and $\mu$ the estimate of the mode of the entire set of PAPs.

In optional step 214, a confidence interval measure of the PAP estimate is evaluated, for example, using confidence interval evaluator 120 (FIG. 1A). The confidence interval measure may be evaluated for a predetermined number of PCG and corresponding ECG signals. In this embodiment, for a predetermined number of acquired PCG and ECG signals, a standard uncertainty is determined as described above.

If a plurality of PAP estimates are generated, a frequency distribution of the PAP estimates may be determined. A fixed interval, for example, about 10 mmHg, around the mode of the plurality of PAP estimates may be used to evaluate the confidence interval measure. For example, the mode PAP estimate, upper and lower limits of the fixed interval and the confidence interval measure may be presented. The confidence interval measure may be lower for very noisy PCG signals, for example, about 50-60%, and higher for clean PCG signals (i.e. PCG signals substantially uncorrupted by noise), for example, about 90%.

In optional step 216, one or more of the PCG signal, the ECG signal, the extracted diastolic signal, the isolated S2 component, $F_{MAX}$, the PAP estimate and the confidence interval measure may be stored, for example in storage means 126 (FIG. 1A). In optional step 218, one or more of the PCG signal, the ECG signal, the extracted diastolic signal, the isolated S2 component, $F_{MAX}$, the PAP estimate and the confidence interval measure may be displayed, for example on display 122 (FIG. 1A).

Figure 4A:
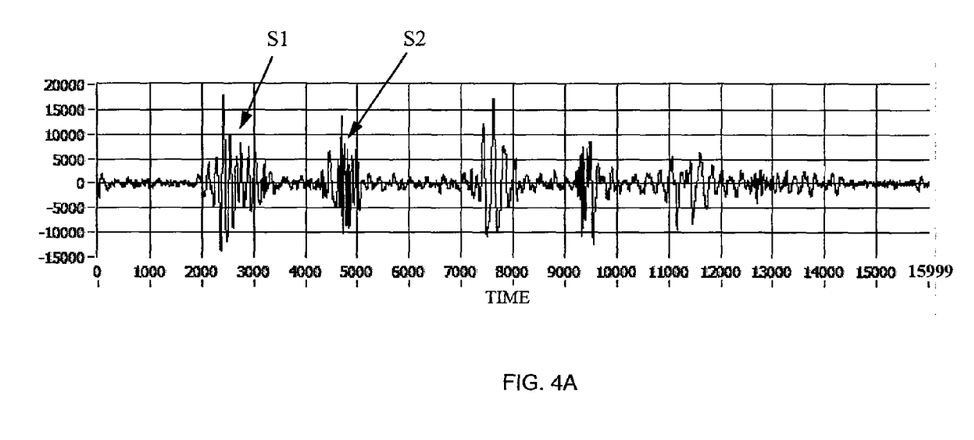
FIG. 4A is a graph of signal amplitude versus time that is useful for illustrating the amplitude of an S2 component according to the exemplary method shown in FIG. 3.
Figure 4B:
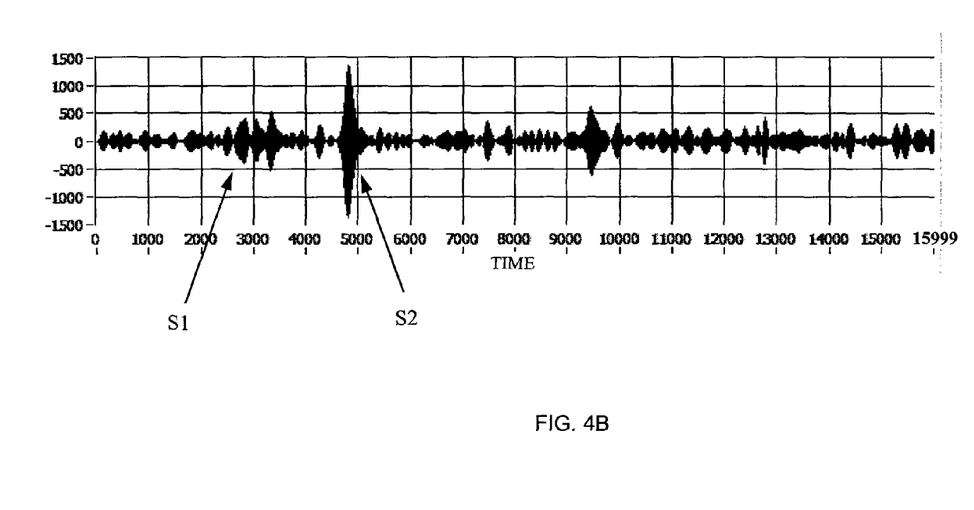
FIG. 4B is a graph of signal amplitude versus time that is useful for illustrating the amplitude of an S2 component after applying a bandpass filter according to the exemplary method shown in FIG. 3.

FIG. 3 is a flow chart illustrating an exemplary method for determining a maximum frequency of an S2 component, according to an embodiment of the present invention. The following figures illustrate examples of the exemplary method shown in FIG. 3: FIG. 4A is a graph of signal amplitude versus time that is useful for illustrating the amplitude of an S2 component; and FIG. 4B is a graph of signal amplitude versus time that is useful for illustrating the amplitude of an S2 component after applying a bandpass filter.

In step 300, an S2 parameter is calculated from the isolated S2 component (step 208 of FIG. 2), for example, by ratio calculator 128 (FIG. 1B). As described above, the S2 parameter is a measure that is associated with an amplitude of the isolated (i.e., the non filtered) S2 component.

In step 302, the lower cutoff frequency, $F_{LOW}$, is initialized, for example, for bandpass filter 130 (FIG. 1B). In step 304, the bandpass filter having cutoff frequencies ($F_{LOW}$, $F_{HIGH}$) is applied to the isolated S2 component, for example, by bandpass filter 130 (FIG. 1B). Initially, the filtered S2 component may be composed substantially of noise, with substantially little contribution from the spectrum of the S2 component. As $F_{LOW}$ is decreased, however, more of the S2 component spectrum may contribute to the filtered S2 component amplitude, causing the filtered S2 parameter to increase.

In step 306, a filtered S2 parameter is calculated from the filtered S2 component, for example, by ratio calculator 128 (FIG. 1B). As described above, the filtered S2 parameter is a measure associated with an amplitude of the filtered S2 component. Referring to FIGS. 4A and 4B, in FIG. 4A, an amplitude of a PCG signal versus time is shown, including a first heart sound (S1) component and an S2 component, within a first frequency range of 30-400 Hz (where the first frequency range is used to illustrate the spectral content of the S2 component). In FIG. 4B, the same PCG signal is shown after applying a bandpass filter for a second frequency range of 288-400 Hz. Comparing FIG. 4B with FIG. 4A, the amplitude of the filtered S2 component in FIG. 4B is about 10 times lower than the S2 component in FIG. 4B.

Referring back to FIG. 3, in step 308, a ratio between the S2 parameter and the filtered S2 parameter is calculated, for example by ratio calculator 128 (FIG. 1B). In step 310, it is determined whether the ratio is less than or equal to a predetermined threshold, for example, by $F_{LOW}$ frequency controller 132 (FIG. 1B). If the ratio is greater than the predetermined threshold, step 308 proceeds to step 312 to reduce $F_{LOW}$ by a predetermined frequency increment, i, and steps 304-310 are repeated.

If it is determined that the ratio is less than or equal to the predetermined threshold, step 310 proceeds to step 314. In step 314, the maximum frequency FMAX is set to the currently selected $F_{LOW}$, for example, by $F_{LOW}$ frequency controller 132 (FIG. 1B), and the process is complete.

Although in an exemplary embodiment, the predetermined threshold is about 10, it is contemplated that the predetermined threshold may be between about 5-15. It is contemplated that a suitable threshold may be selected according to a desired accuracy of the maximum frequency. Although a ratio between the S2 parameter and the filtered S2 parameter is described above, it is understood that an inverse ratio (i.e., a ratio between the filtered S2 parameter and the S2 parameter) may be computed and compared to a corresponding threshold. It is contemplated that any suitable amplitude comparison between the filtered S2 component and the isolated S2 component may be used in order to estimate a maximum frequency of the S2 component.

Although in an exemplary embodiment, the frequency increment is about 1-2 Hz, the frequency increment may be up to about 10 Hz. It is understood that as the frequency increment increases, the accuracy of $F_{MAX}$ may decrease. It is contemplated that any suitable frequency increment may be selected according to a desired accuracy of the maximum frequency.

As described above, a predetermined number of PCG signals and corresponding ECG signals may be acquired and a PAP estimate may be determined from the plurality of acquired sets of signals. Referring now to FIG. 5, an exemplary embodiment is illustrated for generating a PAP estimate from the plurality of acquired sets of signals.

Figure 5:
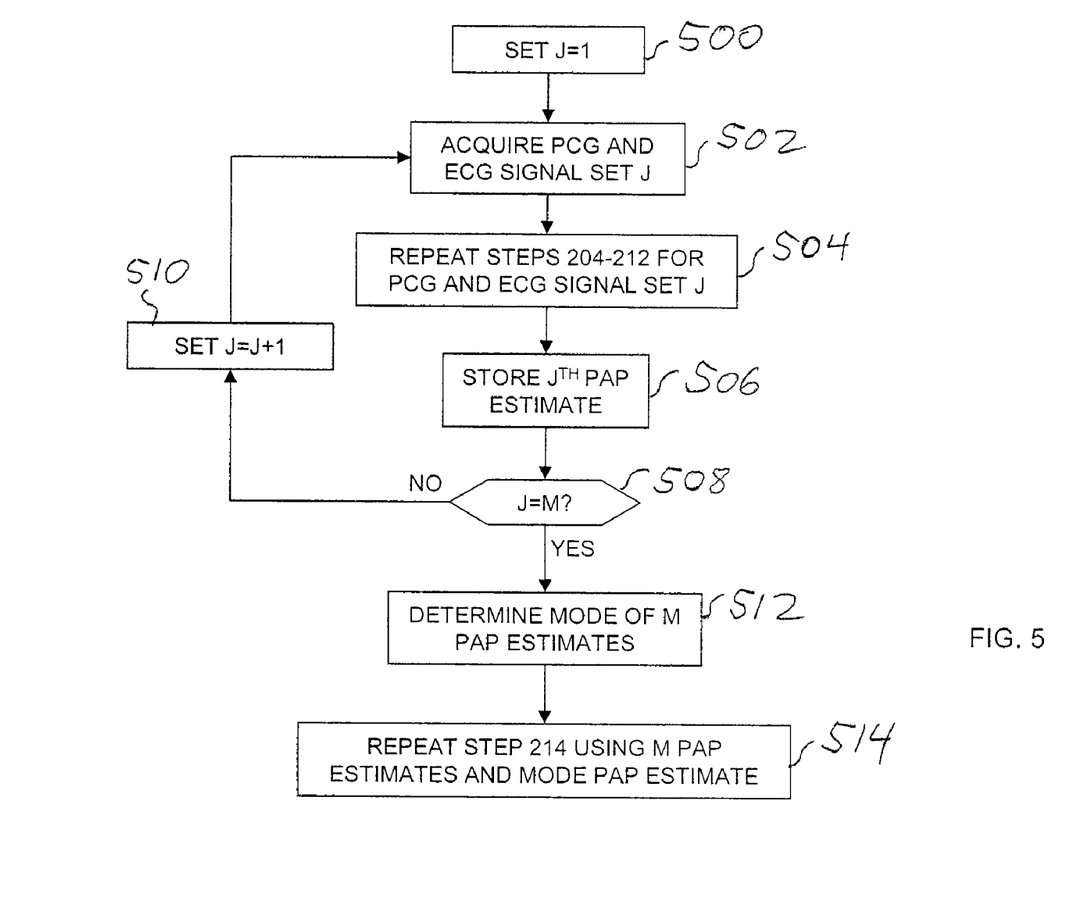
FIG. 5 is a flow chart illustrating an exemplary method for generating a PAP estimate using a plurality of acquired phonocardiogram (PCG) and electrocardiogram (ECG) signals, according to a further embodiment of the present invention.

FIG. 5 is a flow chart illustrating an exemplary method for generating a PAP estimate using a plurality of acquired PCG and ECG signals, according to an embodiment of the present invention. In step 500, a variable J is initialized. The variable J represents a $J^{th}$ signal set of the predetermined number, M, of PCG and corresponding ECG signals to be acquired. In step 502, PCG and ECG signal set J are synchronously acquired, for example using PAP analyzer 108 or, optionally, data acquisition system 106 (FIG. 1A). In step 504, steps 204-212 (FIG. 2) are repeated using PCG and ECG signal set J in order to generate a $J^{th}$ PAP estimate corresponding to signal set J. In step 506, the $J^{th}$ PAP estimate is stored, for example using storage means 126 (FIG. 1A).

In step 508, it is determined whether the predetermined number M of signal sets have been acquired and processed. If fewer than M signal sets have been acquired, step 508 proceeds to step 510 to update the signal set variable J and steps 502-508 are repeated.

If the predetermined number M of signal sets have been acquired and processed, step 508 proceeds to step 512. In step 512, a mode PAP estimate is determined from the M stored PAP estimates. In step 514, step 214 is repeated to determine a confidence interval measure using the mode determined in step 512 and the M PAP estimates, using a frequency density as described above. It is contemplated that any of steps 216-218 may be repeated to store or display desired values and signals.

Although the invention has been described in terms of apparatus and methods for noninvasively estimating a PAP, it is contemplated that one or more components may be implemented in software on microprocessors/general purpose computers (not shown). In this embodiment, one or more of the functions of the various components may be implemented in software that controls a general purpose computer. This software may be embodied in a computer readable carrier, for example, a magnetic or optical disk, a memory-card or an audio frequency, radio-frequency, or optical carrier wave.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for noninvasively estimating a blood pressure, the method comprising:
    a) applying a bandpass filter to a second heart sound (S2) component to generate a filtered S2 component, the bandpass filter having a lower cutoff frequency greater than a maximum frequency of the S2 component;
    b) estimating the maximum frequency of the S2 component using the filtered S2 component;
    c) applying a predetermined relationship between the estimated maximum frequency and blood pressure to generate a blood pressure estimate; and
    d) displaying the blood pressure estimate,
    wherein step (b) includes:
    (b1) calculating a ratio between the S2 component and the filtered S2 component;
    (b2) decreasing the lower cutoff frequency and repeating steps (a) and (b1) with the decreased lower cutoff frequency to calculate the ratio, the lower cutoff frequency being decreased until the calculated ratio is less than or equal to a predetermined threshold, and
    wherein the decreased lower cutoff frequency is used to define the estimated maximum frequency.

2. The method according to claim 1, wherein each of the S2 component and the filtered S2 component is represented by a respective amplitude value, and
    the amplitude value is calculated from at least one of a root-mean-square (rms) value, a peak value or a mean value of an absolute value.

3. The method according to claim 1, wherein the blood pressure includes a pulmonary artery pressure (PAP) and step (c) includes applying the predetermined relationship between the estimated maximum frequency and PAP to generate a PAP estimate.

4. A computer-readable storage medium including computer program instructions that cause a computer to perform the method according to claim 1.

5. The method according to claim 1, further including, prior to step (a), the steps of:
    extracting a diastolic signal from a phonocardiogram (PCG) signal; and
    isolating the S2 component from the diastolic signal,
    wherein the isolated S2 component is used to generate the filtered S2 component.

6. The method according to claim 5, the step of isolating the S2 component includes:
   integrating at least a portion of the diastolic signal within an integration window to determine a target interval including the S2 component; and
   extracting the S2 component from the diastolic signal using the target interval to form the isolated S2 component.

7. The method according to claim 5, wherein the diastolic signal includes a plurality of diastolic signals and the blood pressure estimate is generated according to the plurality of isolated S2 components of the respective plurality of diastolic signals.

8. The method according to claim 7, further including the steps of:
   repeating steps (a)-(c) over the plurality of isolated S2 components to generate a corresponding plurality of blood pressure estimates; and
   determining a mode of the plurality of blood pressure estimates to generate a mode blood pressure estimate.

9. The method according to claim 8, further including the step of determining a confidence interval measure associated with the plurality of blood pressure estimates and the mode blood pressure estimate.

10. The method according to claim 5, the extracting of the diastolic signal includes the steps of:
    synchronously receiving the PCG signal and an electrocardiogram (ECG) signal; and
    extracting the diastolic signal from the received PCG signal using the received ECG signal.

11. The method according to claim 10, further including the step of storing at least one of the received PCG signal, the received ECG signal, the extracted diastolic signal, the isolated S2 component, the estimated maximum frequency and the blood pressure estimate.

12. The method according to claim 10, wherein step (d) further includes displaying at least one of the received PCG signal, the received ECG signal, the extracted diastolic signal, the isolated S2 component and the estimated maximum frequency.

13. Apparatus for noninvasively estimating a blood pressure, the apparatus comprising:
    means for applying a bandpass filter to a second heart sound (S2) component to generate a filtered S2 component, the bandpass filter having a lower cutoff frequency greater than a maximum frequency of the S2 component;
    means for estimating the maximum frequency of the S2 component using the filtered S2 component;
    means for applying a predetermined relationship between the estimated maximum frequency and blood pressure to generate a blood pressure estimate; and
    means for displaying the blood pressure estimate,
    wherein the means for estimating the maximum frequency includes:
    means for calculating a ratio between the S2 component and the filtered S2 component; and
    means for decreasing the lower cutoff frequency of the bandpass filter responsive to the calculated ratio,
    wherein the lower cutoff frequency is decreased until the calculated ratio is less than or equal to a predetermined threshold, and
    wherein the decreased lower cutoff frequency is used to define the estimated maximum frequency.

14. Apparatus according to claim 13, wherein the blood pressure includes a pulmonary artery pressure (PAP) and the means for applying the predetermined relationship includes means for applying the predetermined relationship between the estimated maximum frequency and the PAP to generate a PAP estimate.

15. Apparatus according to claim 13, the apparatus further comprising:
    means for receiving a phonocardiogram (PCG) signal;
    means for extracting a diastolic signal from the received PCG signal; and
    means for isolating the S2 component in the extracted diastolic signal, the isolated S2 component being provided to the means for applying the bandpass filter.

16. A blood pressure analyzer for noninvasively estimating a blood pressure, the blood pressure analyzer comprising:
    a frequency estimator including:
       an estimator input port configured to receive a second heart sound (S2) component;
       a bandpass filter coupled to the estimator input port and configured to generate a filtered S2 component from the S2 component, the bandpass filter having a lower cutoff frequency greater than a maximum frequency of the S2 component,
       wherein the frequency estimator is configured to estimate the maximum frequency of the S2 component using the filtered S2 component; and
    a blood pressure estimator coupled to the frequency estimator and configured to apply a predetermined relationship between the estimated maximum frequency and blood pressure to generate a blood pressure estimate.

17. The blood pressure analyzer according to claim 16, wherein the frequency estimator further includes:
    a ratio calculator coupled to the estimator input port and the bandpass filter, the ratio calculator configured to calculate a ratio between the S2 component and the filtered S2 component; and
    a frequency controller coupled to the ratio calculator and the bandpass filter, the frequency controller configured to decrease the lower cutoff frequency provided to the bandpass filter responsive to the calculated ratio received from the ratio calculator,
    wherein the frequency controller is configured to decrease the lower cutoff frequency until the calculated ratio received from the ratio calculator is less than or equal to a predetermined threshold, and
    the decreased lower cutoff frequency is used to define the estimated maximum frequency.

18. The blood pressure analyzer according to claim 16, wherein the blood pressure includes a pulmonary artery pressure (PAP) and the blood pressure estimator is configured to generate a PAP estimate by applying the predetermined relationship between the PAP and the estimated maximum frequency.

19. The blood pressure analyzer according to claim 16, further comprising:
    an input port for receiving a phonocardiogram (PCG) signal;
    a diastolic signal extractor coupled to the input port, the diastolic signal extractor configured to extract the diastolic signal from the PCG signal; and
    an S2 component isolator configured to isolate the S2 component from the extracted diastolic signal, based on integration of at least a portion of the extracted diastolic signal,
    wherein the isolated S2 component is provided to the estimator input port of the frequency estimator.

20. The blood pressure analyzer according to claim 19, wherein the input port is further configured to receive an electrocardiogram (ECG) signal corresponding to the PCG signal, and
wherein the diastolic signal extractor is configured to extract the diastolic signal using the corresponding ECG signal.

21. The blood pressure analyzer according to claim 20, further comprising a memory configured to store at least one of the received PCG signal, the received ECG signal, the extracted diastolic signal, the isolated S2 component, the estimated maximum frequency and the blood pressure estimate.

22. The blood pressure analyzer according to claim 20, further comprising a display configured to display at least one of the received PCG signal, the received ECG signal, the extracted diastolic signal, the isolated S2 component, the estimated maximum frequency and the blood pressure estimate.

23. The blood pressure analyzer according to claim 19, wherein the PCG signal includes a plurality of PCG signals, the input port receives the plurality of PCG signals, and
the blood pressure analyzer generates the blood pressure estimate according to the plurality of PCG signals received from the input port.

24. The blood pressure analyzer according to claim 23, further comprising a confidence interval evaluator configured to evaluate a confidence interval measure associated with the blood pressure estimate received from the blood pressure estimator.

* * * * *